United States Patent [19]

Anderson

[11] Patent Number: 5,019,039
[45] Date of Patent: May 28, 1991

[54] FLUID DRAINAGE NEEDLE METHOD OF USE

[76] Inventor: Ronald W. Anderson, 407 S. 19th St., Blair, Nebr. 68008

[21] Appl. No.: 437,025

[22] Filed: Nov. 15, 1989

[51] Int. Cl.$^5$ ............................................. A61M 31/00
[52] U.S. Cl. ...................................... 604/51; 604/164
[58] Field of Search ................................ 604/164–168, 604/51, 171, 272, 326, 900; 128/760, 763, 768

[56] References Cited

U.S. PATENT DOCUMENTS

| | | | |
|---|---|---|---|
| 3,680,562 | 8/1972 | Wittes et al. | 604/168 X |
| 3,860,006 | 1/1975 | Patel | 604/164 |
| 4,016,879 | 4/1977 | Mellor | 604/168 X |
| 4,308,875 | 1/1982 | Young | 128/753 |
| 4,388,076 | 6/1983 | Waters | 604/165 |
| 4,722,725 | 2/1988 | Sawyer et al. | 604/27 |
| 4,810,244 | 3/1989 | Allen | 604/44 |

OTHER PUBLICATIONS

Perfektum Catalog, p. 34B, (undated).

Primary Examiner—John D. Yasko
Assistant Examiner—Adam J. Cermak
Attorney, Agent, or Firm—Zarley, McKee Thomte, Voorhees & Sease

[57] ABSTRACT

A method for draining fluid from between inner and outer body wall linings includes the initial step of providing a fluid drainage needle. The needle, with the cannula portion removably fit on the needle portion, is inserted into the body and through the outer body wall. The insertion is stopped when a flash of fluid from between the inner and outer body wall linings is viewed in the hub of the needle portion. The next step is to slide the cannula portion along the needle portion and into the space between the inner and outer wall linings until the sheath aperture is within the fluid. The needle portion is then removed from the cannula portion and the fluid may be drained through the cannula portion as desired.

1 Claim, 1 Drawing Sheet

FLUID DRAINAGE NEEDLE METHOD OF USE

TECHNICAL FIELD

The present invention relates generally to needles utilized in fluid drainage, and more particularly to an improved fluid drainage needle and its method of use.

BACKGROUND OF THE INVENTION

Thoracentesis is a medical procedure which involves inserting a needle through the thoracic cage into the pleural space between the lung and the chest wall to draw off fluid for diagnostic or therapeutic purposes. The major risk in performing thoracentesis is in the possibility of collapsing the lung.

Collapse of the lung during thoracentesis may occur in at least two different ways. First, upon insertion of the conventional thoracentesis needle, the sharp end of the needle can accidentally puncture the lung, thereby causing collapse. The second risk is during aspiration of fluid. If the opening in the needle is closely adjacent to the lung tissue, the lung tissue can be sucked up against the needle, and the resulting suction against the lining on the lung could cause collapse.

While the specific problems involved with thoracentesis have been described hereinabove, similar problems exist in fluid drainage in related methods, such as pericardiocentesis and paracentesis.

It is therefore a general object of the present invention to provide an improved needle for draining fluid from between two wall linings.

Another object of the present invention is to provide an improved method for draining fluid from between two wall linings.

A further object of the present invention is to provide a fluid drainage needle which substantially eliminates the possibility of puncturing an inner wall lining after passing through an outer wall lining.

Yet another object is to provide a fluid drainage needle which provides an indication to the user when the needle has been introduced into fluid between two wall linings.

Still another object of the present invention is to provide a fluid drainage needle which prevents the suction of the inner wall lining into the needle during fluid drainage.

These and other objects of the present invention will be apparent to those skilled in the art.

SUMMARY OF THE INVENTION

The fluid drainage needle of the present invention includes a cannula portion slidably associated with a needle portion. The needle portion includes a rigid hollow needle mounted on a hollow base with a translucent hollow hub portion on the base for viewing fluid passing through the needle. The cannula portion includes a flexible hollow sheath connected to a hollow hub, the sheath having a blunt distal end. At least one aperture is formed in the side of the sheath approximately one-quarter inch from the distal end and in communication with an interior hollow portion of the sheath. The cannula hub is adapted to selectively removably fit on the needle base with the needle projecting within the sheath. The sheath is of a length slightly less than the length of the needle, so that the sharp end of the needle projects from the sheath when the cannula portion is carried on the needle portion. Preferably, a second aperture is formed in the cannula portion approximately one-half inch from the distal end and in communication with the interior hollow portion of the sheath. This second aperture is preferably located diametric to the first aperture.

The method for draining fluid from between inner and outer body wall linings includes the steps of providing a fluid drainage needle as described above. The needle, with the cannula portion removably fit on the needle portion, is inserted into the body and through the outer body wall. The insertion is stopped when a flash of fluid from between the inner and outer body wall linings is viewed in the hub of the needle portion. The next step is to slide the cannula portion along the needle portion and into the space between the inner and outer wall linings until the sheath aperture is within the fluid. The needle portion is then removed from the cannula portion and the fluid may be drained through the cannula portion as desired.

DESCRIPTION OF THE PREFERRED EMBODIMENT

Figure 1:
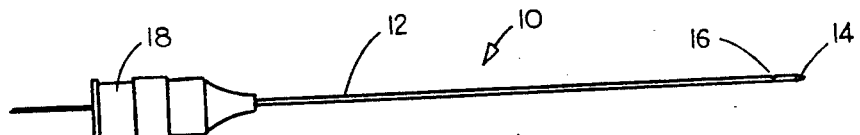
FIG. 1 is an elevational view of a pencil point type fluid drainage needle utilized in the prior art.

Referring now to the drawings, in which identical or corresponding parts are identified with the same reference numeral, and more particularly to FIG. 1, a fluid drainage needle utilized in the prior art is identified generally at 10 and includes a stainless steel cannula 12 with a sharp pencil point end 14. A side hole 16 is located 0.110 inches from the distal end, for draining fluid. The hub portion 18 of needle 10 has a luer lock for connection to a syringe, or the like.

Figure 2:
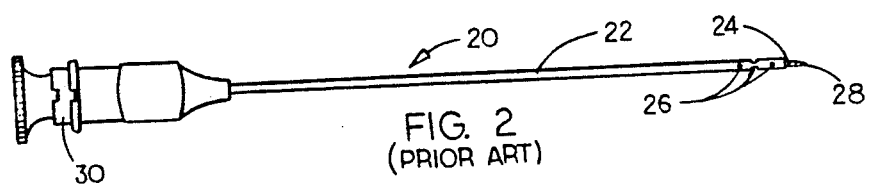
FIG. 2 is an elevational view of a prior art thoracentesis needle.
Figure 3:
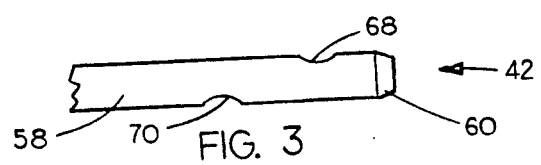
FIG. 3 is an enlarged view of the distal end of the cannula portion of FIG. 4.

Referring now to FIGS 2 and 3, a second type of thoracentesis needle utilized in the prior art is identified general at 20 and includes a stainless steel cannula 22 with a tapered blunt end 24. Three holes 26, having a diameter of 0.036 inch, are formed within ⅛ inch of the distal blunt end 24. A fitted trocar stylet 28 extends approximately 5/32 of an inch from the distal end 24 of cannula 22. The hub 30 connected to stylet 28 includes a luer lock for connection to a syringe or the like.

Figure 4:
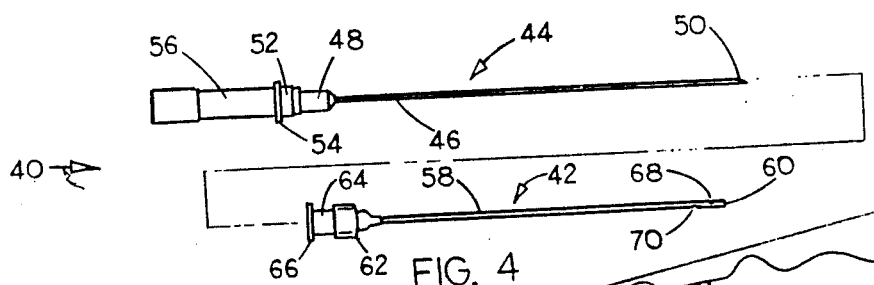
FIG. 4 is an exploded sectional view through the fluid drainage needle of the present invention.

Referring now to FIG. 4, the fluid drainage needle of the present invention is identified generally at 40, and includes a clear plastic cannula portion 42 and a needle portion 44. Needle portion 44 includes a rigid stainless steel hollow needle 46 mounted to a hollow base 48 such that fluid may pass therethrough. The distal end 50 of needle 46 is beveled to allow for easier insertion. Needle base 48 is mounted to a clear plastic hollow hub 52 which has a projecting ring 54 thereon for gripping by the user. Hub 52 is designed for a tight fitted removable connection to a hollow shank 56. Shank 56 is designed for connection to an IV tube or the like. Hub 52 may also be directly connected to a syringe or the like, if desired.

Cannula portion 42 includes a flexible clear plastic hollow sheath 58 having a tapered blunt end 60. Flexible sheath 58 is fastened to a rigid hollow hub 62, such that fluid passing through sheath 58 will be directed through hub 62. Sheath hub 62 includes a hollow tubular portion 64 of a length in diameter designed to fit snugly over needle base 48 on needle portion 44. An annular projecting flange 66 is formed on the end of tubular portion 64 to assist in gripping the cannula portion and removing it from needle portion 44.

Approximately ¼ inch from the distal end 60 of plastic sheath 58, an aperture 68 is carved into one side of the cylindrical sheath. Preferably, aperture 68 is approximately 1/16 inch in diameter. A second aperture 70 is carved in sheath 58 diametric to first aperture 68, and approximately ¼ inch farther from distal end 60. Thus, aperture 70 is approximately ½ inch from distal end 60. Aperture 70 is also approximately 1/16 inch in diameter. The location of apertures 68 and 70 is important, since orienting the apertures any closer together has a tendency to cause the flexible plastic sheath 58 to bend and collapse between the apertures. Similarly, the use of additional apertures, or apertures located other than diametric to one another, also increases the risk of collapse of the flexible sheath 58. As discussed in more detail hereinbelow, flexible sheath 58 is preferably slightly shorter in length than needle 46, such that needle's beveled end 50 projects beyond the tapered blunt end 60 of sheath 58.

Figure 5:
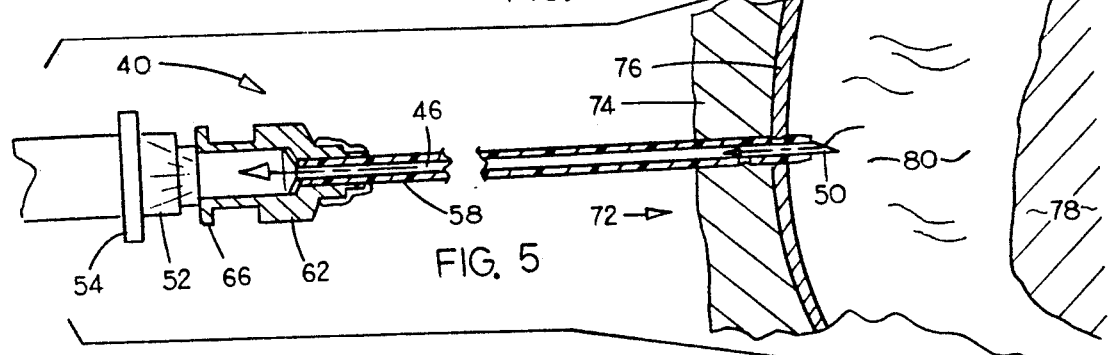
FIG. 5 is a partial sectional view showing an initial step in utilizing the needle of the present invention.
Figure 6:
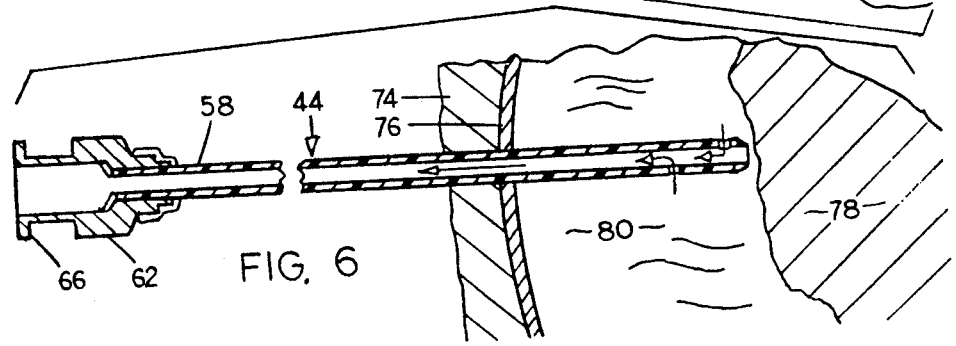
FIG. 6 is a partial sectional view showing the step of draining fluid utilizing the needle of the present invention.

Referring now to FIGS. 5 and 6, the method of use of the fluid drainage needle of this invention is described in more detail. A sectional view through a portion of a body 72 is shown with needle 40 projecting through the chest wall 74 and thence through an outer lining 76 into the pleural space between the lung 78 and lining 76. A fluid 80 located between lung 78 and lining 76 is the subject of the medical procedure for which needle 40 was designed.

While needle 40 may be attached to a syringe 82 to perform the procedure, a syringe is not required. In this case, clear plastic hub 52 is connected to the end of syringe 82 in a conventional fashion. With the cannula portion 42 mounted on needle portion 44, needle 40 is inserted through chest wall 74 until the distal end 50 passes through lining 76 and into the pleural space. Fluid 80 from pleural space is brought up through the needle and will pass into the clear plastic hub. This flash of fluid indicates that the tip of the needle is in the appropriate position in the pleural space. While holding onto needle hub 52, cannula portion 58 is slid slightly forward by pushing on cannula hub 64 using flange 66. Once sheath 58 is moved a distance so as to encase needle top 50, needle portion 44 is removed from cannula portion 42. Cannula portion 42 may then be attached to a tube or other device for collecting fluid drained from the pleural cavity.

As fluid drains from the pleural space, and the lung 78 draws closer to lining 76, the blunt end 60 of sheath 58 may contact the lung wall. Apertures 68 and 70 are provided to prevent the suction that occurs during aspiration of the fluid from sucking the lung wall into the blunt end 60 and possibly collapsing the lung. Furthermore, the flexible plastic material utilized in sheath 58 allows the sheath 58 to be maneuvered between the lung 78 and lining 76 without fear of puncturing the lung with a sharp point. In fact, sheath 58 may be bent to an arcuate shape so as to more closely follow the lung and lining, and thereby aspirate more fluid than a conventional rigid thoracentesis needle.

Whereas the invention has been shown and described in connection with the preferred embodiment thereof, it will be understood that many modifications, substitutions and additions may be made which are within the intended broad scope of the appended claims. For example, needle 40 and its method of use may be utilized in other situations where removal of a fluid between two linings is required. More specifically, the invention is most advantageously utilized wherein the fluid to be removed lies between an inner wall lining which may be punctured utilizing conventional fluid drainage needles, such as in pericardiocentesis or paracentesis.

Therefore, there has been shown and described an improved fluid drainage needle and its method of use, which accomplishes at least all of the above stated objects.

I claim:

1. A method for draining fluid from between inner and outer body wall linings, comprising the steps of: providing a fluid drainage needle, including:
   a cannula portion selectively, slidably associated with a needle portion;
   said needle portion including:
      a rigid hollow needle mounted on a hollow base, said needle having a sharp distal end; and
      a translucent hollow hub portion mounted to said base, for viewing fluid passing therethrough;
   said cannula portion including a flexible, hollow sheath connected to a hollow hub, said sheath having a blunt distal end;
   said sheath having at least one aperture formed in its side approximately ¼ inch from the distal end, and in communication with the interior hollow portion of the sheath, the aperture of a diameter sufficient to permit fluid aspiration therethrough;
   said cannula hub being adapted for a selectively removable fit on said needle base with the needle projecting within said sheath;
   said sheath of a length slightly less than said needle, such that the sharp end of said needle projects from said sheath when said cannula portion is carried on said needle portion;
inserting said needle, with said cannula portion removably fit on said needle portion, into a body and through said outer body wall;
stopping the insertion step when a flash of fluid from the between the inner and outer body wall linings is viewed in the needle portion hub;
sliding the cannula portion along the needle portion and into the space between the inner and outer wall linings until the sheath aperture is within the fluid;
removing the needle portion from said cannula portion;
draining the desired amount of fluid from between said inner and outer linings; and
removing said cannula portion.

* * * * *